United States Patent [19]

Worrell et al.

[11] 4,428,770

[45] Jan. 31, 1984

[54] METHODS OF MANUFACTURING METAL FROM A MELT, DETERMINATION OF SULFUR AND CARBON THEREIN, SENSORS THEREFOR AND SOLID ELECTROLYTE COMPOSITIONS FOR SAID SENSORS

[75] Inventors: Wayne L. Worrell, Narberth; Qing-Guo Liu, Philadelphia, both of Pa.

[73] Assignee: University Patents, Inc., Norwalk, Conn.

[21] Appl. No.: 351,473

[22] Filed: Feb. 23, 1982

[51] Int. Cl.³ .................. G01N 27/58; C04B 35/48; C04B 35/51
[52] U.S. Cl. ................................... 75/45; 75/76; 204/1 T; 204/421; 204/422; 266/99; 501/87; 501/104; 501/108; 501/123; 501/152
[58] Field of Search ............... 501/87, 152, 104, 108, 501/123; 204/195 S, 1 K, 1 F, 421, 422, 423; 266/99; 75/76, 45

[56] References Cited

FOREIGN PATENT DOCUMENTS 1523030 6/1969 Fed. Rep. of Germany ...... 204/1 T
1211957 11/1970 United Kingdom ............. 204/1 T

OTHER PUBLICATIONS

"Developing New Electrochemical Sensors," Worrell, *Proceedings of the Symposium on Metal-Slag-Gas Reaction and Processes*, Electrochemical Society, Princeton (1975).
"Oxide Solid Electrolytes", Worrell, *Topics in Applied Physics*, Geller Ed., Springer (1977).
"The Measurement of Oxygen Chemical Potentials for the Calcium Fluoride Solid Electrolyte," Worrell et al., J. of Electrochemical Society, vol. 126, No. 8, pp. 1360-1363, (1979).
"The Measurement of Sulfur Chemical Potential Differences Using a Calcium Fluoride Solid Electrolyte," Worrell et al., J. of Electrochemical Society: Electrochemical Science and Technology, pp. 1717-1721, Aug. 1980.
"Galvanic-Cell Investigation with a $CaF_2$ Solid Electrolyte at Elevated Temperatures", Worrell, Solid State Ionics 3/4, pp. 559-563, (1981).
"Development of the High-Temperature Solid-Sulfide Electrolyte", Worrell et al., *High Temperature Technology*, IUPAC, pp. 503-509, (1969).
Abstract to the 110th Annual Meeting of the A.I.M.E., Feb. 23-25, 1981, *J. of Metals*, (Dec. 1980).

*Primary Examiner*—G. L. Kaplan
*Attorney, Agent, or Firm*—Woodcock, Washburn, Kurtz, Mackiewicz & Norris

[57] ABSTRACT

Materials, methods and articles for the electrochemical determination of sulfur and carbon in fluids are provided. In accordance with a preferred embodiment, an electrolyte is furnished comprising a solid solution of an oxide of either zirconium, thorium or hafnium together with an oxide of an element of groups IIA or IIIB of the periodic table of the elements together with a sulfide or carbide of an element of groups IIA or IIIB of the periodic table. Processes employing such electrolytes together with articles incorporating them are also contemplated.

66 Claims, 1 Drawing Figure

METHODS OF MANUFACTURING METAL FROM A MELT, DETERMINATION OF SULFUR AND CARBON THEREIN, SENSORS THEREFOR AND SOLID ELECTROLYTE COMPOSITIONS FOR SAID SENSORS

BACKGROUND OF THE INVENTION

This invention deals with the determination of sulfur and carbon in fluids. More particularly, materials, methods and articles have now been discovered which permit the electrochemical determination of sulfur or carbon in diverse fluids, especially in melts. Even more particularly, means have now been discovered for the measurement of the concentration of sulfur or carbon in molten metals such as in molten copper and steel. It is believed that electrochemical cell measurement of sulfur or carbon in fluids has heretofore been impossible.

Electrochemicals sensors adapted for the measurement of oxygen in liquids such as in metallurgical melts are known. See in this regard "Developing New Electrochemical Sensors," Worrell, *Proceedings of the Symposium on Metal-Slag-Gas Reaction and Processes*, Electrochemical Society, Princeton (1975); "Oxide Solid Electrolytes," Worrell, *Topics in Applied Physics*, Geller Ed., Springer (1977); and "The Measurement of Oxygen Chemical Potentials for the Calcium Fluoride Solid Electrolyte," Worrell et.al., Journal of the Electrochemical Society, Vol. 126, No. 8, pp. 1360–1363 (1979). The foregoing references are incorporated herein by reference in order to describe more fully the electrochemical determination of elemental compositions employing solid electrolyte sensors. The foregoing publications disclose the employment of certain simple solid solutions such as those of zirconium oxide and thorium oxide in the electrochemical detection of oxygen. Electrolytes suitable for the electrochemical measurement of sulfur or carbon under laboratory conditions have been disclosed. Calcium fluoride, for example, has been proposed for such use. See "The Measurement of Sulfur Chemical Potential Differences Using a Calcium Fluoride Solid Electrolyte," Worrell et.al., Journal of the Electrochemical Society: Electrochemical Science and Technology, pp. 1717–1721, August 1980; and "Galvanic-Cell Investigation With a $CaF_2$ Solid Electrolyte at Elevated Temperatures," Worrell, Solid State Ionics 3/4, pp. 559–563 (1981). Further attempts at the electrochemical measurement of sulfur have been reported. Thus, the employment of calcium-sulfide-based electrolytes is reported in "Development of the High-Temperature Solid-Sulfide Electrolyte," Worrell et.al., *High Temperature Technology, IUPAC*, pp. 503–509 (1969). Employment of barium carbide-barium fluoride solutions for measurement of carbon has also been reported. Each of the foregoing methods and materials proposed for the measurement of sulfur or carbon in electrochemical cells has met with severe practical limitations. For example, calcium fluoride-based electrolytes, such as calcium fluoride-calcium sulfide can be used successfully to measure sulfur potentials at temperatures between 500° and 950° C., however such electrolytes will not function in oxidizing environments "presumably due to the formation of an oxide coating." See the solid State Ionics article referred to above.

Other systems for the measurements of sulfur including $CaS(Y_2S_3)$, $K_2SO_4$, $Na_2SO_4$, $Na_2SO_4$ (5% $Ag_2SO_4$) and others have been studied. Each of those proposed suffer from drawbacks such as instability to oxygen and/or water or disproportionation in the presence of high sulfur concentration. At the present time, no electrochemical cell system for the determination of sulfur or carbon in fluids is known.

OBJECTS OF THE INVENTION

It is an object of the present invention to provide electrochemical sensors for the measurement of sulfur and/or carbon in fluids.

It is a further object to provide methods for the detection of sulfur and carbon in fluids.

A further object is to provide apparatus for the measurement of sulfur and carbon in such fluids.

Yet another object is to furnish a method for the determination of sulfur and carbon in metallurgical melts such as in molten copper or steel.

A still further object is to provide novel compositions which are suitable for use as electrolytes in the determination of sulfur and carbon in fluids.

It is yet another object to provide such compositions, apparatus and methods which are suitable for the detection and measurement of sulfur or carbon in fluids having substantial proportions of oxygen therein.

A further object is to provide such methods, articles and apparatus which are useful in the detection of carbon or sulfur in the presence of substantial proportions of oxygen.

These and other objects will be apparent from a review of the present specification.

SUMMARY OF THE INVENTION

Figure 1:
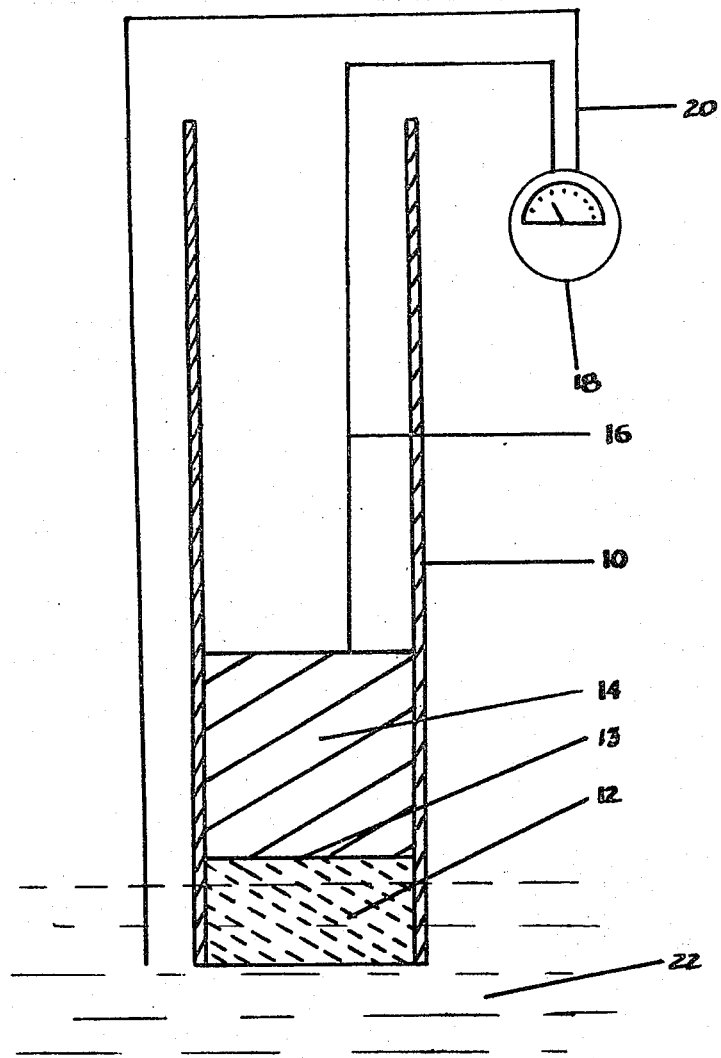
FIG. 1 is a representation of a galvanic cell useful in the detection of sulfur or carbon in fluids. As depicted, the galvanic cell is electrically connected to a potential sensing means which assists in the determination.

It has been discovered that electrolytes comprising a solid solution comprising from about 75 to about 98 mole percent of zirconium dioxide or thorium dioxide together with from about 1 to about 20 mole percent of calcium oxide or another oxide of an element from either of groups IIA or IIIB of the periodic table of the elements and from about 1 to about 20 mole percent of calcium sulfide or of another sulfide of groups IIA or IIIB of the periodic table may be formulated having a sensible electrochemical potential towards sulfur in a fluid even when the fluid has a substantial oxygen concentration therein. Substitution of calcium carbide or of a carbide of another element from group IIA or IIIB of the periodic table for the sulfide component of the solid solution yields an electrolyte which is suitable for the determination of carbon in such fluids. According to a preferred embodiment of the present invention, the detection of sulfur or carbon in a fluid is accomplished by contacting the fluid with one of the foregoing electrolytes.

The foregoing electrolytes may be embodied in apparatuses adapted for the measurement of sulfur or carbon content in a fluid. In such a case, it is preferred to combine the foregoing electrolyte with a reference electrode in contact therewith and to provide suitable electrical contacts together with electrical potential sensing means in association therewith for the quantification of the sulfur or carbon in the fluid.

In view of the importance to the metallurgical industries of the careful determination of sulfur and carbon contents in metallurgical melts, it is now possible to manufacture metals employing processes which comprise monitoring the level of sulfur or carbon in molten metal prior to casting and, optionally, to modify the composition of such melts in response to the monitoring.

DETAILED DESCRIPTION OF THE INVENTION

The electrolytes which have been found to be useful for the measurement of sulfur in fluids according to the present invention comprise solid solutions of metallic species. More particularly, such solutions comprise, in major proportion, a metal oxide whose crystal structure is face-center-cubic in the manner of fluorite. The solid solutions further comprise minor proportions of an oxide of an element of groups IIA or IIIB of the periodic table of the elements together with a minor proportion of the sulfide of an element of groups IIA or IIIB of the periodic table.

Electrolytes for the detection of carbon in fluids may also be formulated according to this invention. Thus, substitution of a minor proportion of the carbide of an element of groups IIA or IIIA of the periodic table is made for the sulfide employed in sulfur sensing electrolytes.

The metallic oxide having a fluorite crystal structure is preferably an oxide of a metal selected from the group consisting of zirconium, thorium or hafnium and mixtures thereof. The foregoing oxides are known, respectively, as zirconia, thoria, and hafnia. Zirconia and thoria are preferred compositions and are presently believed to be the best oxides for use in the preparation of electrolytes in accordance with the present invention.

The foregoing metallic oxides having a fluorite crystal structure are present in the solid solutions of the present invention in major proportion. It is preferred that such materials comprise from about 75 mole percent to about 98 mole percent of the solutions. It is still more preferred that such metal oxides comprise from about 85 to about 96 mole percent of the electrolyte.

The solid solutions of the present invention further comprise an oxide of an element of either of group IIA or IIIB of the of the periodic table of the elements. Of the foregoing, magnesium, calcium strontium, barium, scandium, yttrium and lanthanum oxides and mixtures thereof are preferred. Of the foregoing, calcium oxide is most preferred and believed to be the best material for employment in the preparation of the electrolytes of this invention.

The oxide of an element of groups IIA or IIIB of the periodic table is present in amounts of about 1 to about 20 mole percent in the solid solutions of this invention. It is preferred that amounts of from about 2 to about 10 mole percent be employed and even more preferred that the solid solutions comprise from about 4 to about 6 mole percent of this component.

Electrolytes for the determination of sulfur in fluids further comprise a sulfide of an element of groups IIA or IIIB of the periodic table of the elements. Accordingly, magnesium sulfide, calcium sulfide, strontium sulfide, barium sulfide, scandium sulfide, yttrium sulfide, lanthanum sulfide and mixtures thereof are preferred with calcium sulfide being most preferred. Calcium sulfide is believed to be the best material for employment in the present invention for the detection of sulfur. While it is not believed to be necessary to employ oxides and sulfides having the same element of groups IIA or IIIB of the periodic table, such employment is convenient and is presently preferred.

The sulfide is included in the compositions of this invention in amounts of from about 1 to about 20 mole percent. It is preferred that amounts of from about 2 to about 10 mole percent be employed, while amounts of about 4 to about 6 mole percent are most preferred.

Electrolytes for the detection of carbon in fluids are similar to those useful for the detection of sulfur except that a carbide rather than a sulfide of an element of groups IIA or IIIB of the periodic table of the elements is included in the solid solutions designed for carbon detection. Accordingly, magnesium carbide, calcium carbide, strontium carbide, barium carbide, scandium carbide, yttrium carbide, lanthanum carbide and mixtures thereof are preferred for employment in carbon-sensing electrolytes. Calcium carbide is most preferred.

The foregoing carbides are employed in amounts of from about 1 to about 20 mole percent of the solid solution. It is preferred to employ such carbides in amounts of from about 2 to about 10 mole percent and even more preferred to employ from about 4 to about 6 percent thereof in such solutions.

Presently preferred solid solution compositions for the electrolytes of this invention employ from about 75 to about 98 mole percent of zirconium, or thorium dioxide, from about 1 to about 20 mole percent of calcium oxide, and from about 1 to about 20 mole percent of calcium sulfide or calcium carbide depending upon whether the detection of sulfur or carbon is desired. Still more preferred are compositions having about 90 mole percent of zirconium dioxide or thorium dioxide together with about 5 mole percent of calcium oxide and about 5 mole percent of either calcium sulfide or calcium carbide.

Numerous other materials, such as other oxides, silicates and other species may be included in the compositions of the present invention without deviating from its spirit. All such inclusions are in addition to the mole percentages specified for the principal components of the solid solutions.

The preparation of the solid solutions useful for employment as electrolytes in the present invention may be accomplished by any of the methods which are well known to those skilled in the art who are familiar with the preparation of solid solutions. According to a preferred method for the production of such electrolytes, the components of the electrolyte are selected and powders thereof mixed together in proper proportions. It is generally necessary to ensure that each of the components are dry and free from substantial impurities. It is preferred that the mixture be pre-pressed under high pressure such as about 20,000 psi and the resulting pellets granulated. The resulting powder is then pelletized under pressure into the desired conformation. The pellets are then preferably sintered at, for example, from about 1200° to about 1800° C. in partial vacuum/argon. The resulting sintered bodies are useful as electrolytes in apparatus for the measurement of sulfur or carbon in fluids.

Certain sulfides, such as calcium sulfide, have a finite vapor pressure at elevated temperatures. Accordingly a certain quantity of such sulfides may be lost during sintering of the electrolytes of the present invention. For clarity, compositional ranges referred to herein relate to dry weight before sintering.

Apparatus may be designed employing the novel electrolytes of the present invention for the measurement of sulfur or carbon in fluids. In this regard, apparatus similar to that disclosed in "Oxide Solid Electrolytes", Worrell, *Topics in Applied Physics,* Vol 21, Chapter 6, Geller Ed. Springer (1977) is preferred. FIG. 1 is a schematic representation of such preferred apparatus. Holder means 10 is preferably provided for the electrolyte of the present invention, which holder means may conveniently comprise a silica tube or other heat resistant material. A body of electrolyte in accordance with the present invention 12 is placed in the holder 10 and firmly attached thereto, preferably by bonding in place. According to a preferred embodiment, a reference electrode material 14 is placed in contact with electrolyte 12 to form a boundary 13. First electric contact means 16 is preferably provided which is preferably adapted for electrical connection with electric potential measuring means 18. Second electric contact means 20 is also preferably provided being adapted for electrical connection with said electric potential measuring means 18. The second electric contact means is preferably also adapted for making contact with the fluid to be measured and tested 22.

In practice, the electrolyte 12 is placed in contact with the fluid to be measured or tested 22. Electrical contact means 20 is also brought into contact with said fluid 22. By judicious choice of electrolyte material 12 and reference electrode material 14, contact of the apparatus of this invention with the fluid to be tested 22 will result in the electric potential being generated between the fluid 22 and the reference electrode 14, said potential being related to the individual half cell electrochemical potentials generated at the electrolyte-electrode boundry 13 and at the interface of electrolyte 12 and fluid to be tested 22. The foregoing electric potential can be measured through potential measuring means 18.

It is preferred that reference electrode material 14 be isolated from the fluid to be tested 22 by virtue of the geometric arrangement of said reference material internal to holder 10 and the electrolyte 12. It should be understood that the foregoing description of the apparatus preferred for employment in the present invention is intended to be schematic and illustrative only. Those skilled in the art will readily appreciate that additional geometric arrangements of elements may be employed in expression of the spirit of the present invention.

Methods for detection of sulfur or carbon in a fluid are now possible employing the novel electrolytes of the present invention. Accordingly, such processes comprise contacting the fluid to be tested with one of the foregoing electrolytes. It is preferred that the electrolyte be coupled with a reference electrode material. Accordingly, such reference electrode is preferably placed in contact with the electrolytes of this invention and that the resulting assembly be provided with holder means for convenient contacting of the fluids to be tested.

It is to be understood that each of the electrolytes which have been disclosed herein as being useful in the practice of one or more embodiments of the present invention may be employed with the processes hereof for the detection of sulfur or carbon in fluids. It should be further understood that the foregoing electrolytes maybe so employed even when the fluid to be tested comprises substantial quantities of oxygen and/or water vapor as constituents. When such oxygen or water vapor is present in the fluid to be tested, it has been found to be preferred to provide a reference electrode which serves to minimize interference by such oxygen or water vapor or to provide a compensatory electrical potential due to their presence. Such reference electrodes are well known to those skilled in the art. A substantial quantity of oxygen in accordance with the present invention will vary with the fluid to be tested and may be as low as, for example, 1 p.p.m. in some systems.

Preferred reference electrodes for the detection of sulfur comprise solid solutions of a metal and its metallic sulfide. Preferred reference electrodes for the detection of carbon employ solid solutions of a metal and its metallic carbide. Most preferred are reference electrode solutions according to the foregoing wherein the metal is an element of groups VIB or VIIB of the periodic table of the elements. Even more preferred for the detection of sulfur are reference electrodes comprising solid solutions of tungsten-tungsten sulfide, chromium-chromium sulfide, and manganese-manganese sulfide. For the detection of carbon, reference electrodes comprising solid solutions of tungsten-tungsten carbide; chromium-chromium carbide; or manganese-manganese carbide are preferred.

In accordance with a preferred embodiment of the present invention, methods for the detection of sulfur in fluids having a substantial content of oxygen are provided comprising selecting an electrolyte having a sensible electrochemical potential for sulfur in said fluid, providing in contact with said electrolyte a reference electrode having a fixed electrochemical potential, providing an electrochemical contact with each of said reference electrode and said fluid, providing an electric potential measurement means, contacting said fluid with said electrolyte to generate an electric potential, and measuring the electric potential thus generated with the electric potential measuring means. A similar process for the detection of carbon employs an electrolyte having a sensible electrochemical potential for carbon in said fluid.

According to the present invention, an apparatus for the detection of sulfur in a fluid may be provided comprising a solid electrolyte having a sensible electrochemical potential for sulfur in the fluid together with a reference electrode having a fixed electrochemical potential in contact with the solid electrolyte. A similar apparatus for the detection of carbon may also be formulated with the employment of a solid electrolyte having a sensible electrochemical potential for carbon in the fluid.

The foregoing materials, processes and apparatus are adapted for the measurement of sulfur or carbon in a wide variety of fluids including those fluids having a substantial portion of oxygen therein. Accordingly, the present materials, apparatus, and processes may be adapted for a wide variety of gaseous and liquid fluids. A particular area of utility of the foregoing materials, apparatus and processes is in the area of metallurgical melts. By virtue of the fact that the foregoing electrolytes are solid solutions, they are stable in metallurgical melts at high temperature. Accordingly, the measurement of suflur or carbon in such metallurigcal melts, such as in molten copper, brass, bronze, steel, etc., is now possible for the first time.

In view of the foregoing, it is now possible to manufacture metal through a process comprising monitoring the level of sulfur or carbon in molten metal through employment of one of the processes of this invention or through the employment of one or more of the materials or apparatuses thereof. It is now also possible for the first time to provide modification of the metallurgical melt in response to the monitoring of the content of sulfur or carbon therein through one of the products, processes, or apparatus of this invention. Accordingly, metal may be manufactured by preselecting a level of sulfur or carbon desired in the cast metal, monitoring the level of sulfur or carbon in the molten metal prior to casting, and, by modifying the composition of said molten metal in response to the monitoring, attaining cast metal having the preselected level of sulfur or carbon.

Reference is made to additional illustrative material contained in "Development of a Solid Electrolyte to Measure Sulfur Potentials in Oxidizing Environments," Worrell and Liu, *Chemical Metallurgy—a Tribute to Carl Wagner*, A.I.M.E. (1981); as first reported during the 110th Annular Meeting of the A.I.M.E., Feb. 23–25, 1981. The foregoing is incorporated herein by reference.

It is to be understood that the present invention is not limited to the area of metallurgical processing but may be used in many other industrial, laboratory and commercial areas as well.

EXAMPLE 1

90 percent of finely powdered (−325 mesh) thoria powder was mixed with 5.7 mole percent of calcium oxide powder and 4.3 mole percent calcium sulfide powder. The calcium oxide powder had been sintered for 5 hours at 750° C. to remove water vapor and calcium carbonate. The mixture was pre-pressed into pellets at 20,000 psi, which pellets were granulated into −50 mesh particles. The coarse powder was re-pressed into pellets under hydraulic pressure. The pellets were then sintered in a thorium crucible preferably in a furnace employing a tantalum heating element to avoid graphite contamination. While under 700° C., the furnace was maintained in vacuo. Above 700° C., argon was used to blanket the samples. Sintering proceeded for a period of six days with the temperature being varied from about 1300° C. to about 1750° C. on a periodic basis. Cooling was accomplished at a rate of 50° C. per hour to result in sintered electrolyte pellets. The foregoing pellets may be coupled with a reference electrode comprising either tungsten-tungsten sulfide, chromium-chromium sulfide or manganese-manganese sulfide for the detection of sulfur in fluids.

EXAMPLE 2

Zirconium-based electrolyte pellets were produced from about 89 mole percent zirconia, 5 mole percent calcium oxide, and 5 mole percent calcium sulfide together with about 1 mole percent each of alumina and silica. Pellets were pressed, granulated and repressed in accordance with Example 1 at which time they were sintered. The pellets were heated at a rate of 50° C. per hour to 1300° C., at which temperature they were held for 2½ days. The temperature was then raised to 1750° C. and maintained there for an additional three days. The electrolyte pellets were then cooled at a rate of 50° C. per hour to room temperature. Upon opening the sintering furnace, the aroma of sulfur may be detected indicating some loss of calcium sulfide from the compositions. The foregoing pellets may be combined with tungsten, chromium, or manganese-based reference electrodes for the detection of sulfur in molten and other fluids.

What is claimed is:
1. A solid solution of:
 from about 75 mole percent to about 98 mole percent of zirconium dioxide;
 from about 1 mole percent to about 20 mole percent of calcium oxide; and
 from about 1 mole percent to about 20 mole percent of calcium sulfide.
2. A solid solution of:
 from about 75 mole percent to about 98 mole percent of zirconium dioxide;
 from about 1 mole percent to about 20 mole percent of calcium oxide; and
 from about 1 mole percent to about 20 mole percent of calcium carbide.
3. A solid solution of:
 from about 75 mole percent to about 98 mole percent of thorium dioxide;
 from about 1 mole percent to about 20 mole percent of calcium oxide; and
 from about 1 mole percent to about 20 mole percent of calcium sulfide.
4. A solid solution of:
 from about 75 mole percent to about 98 mole percent of thorium dioxide;
 from about 1 mole percent to about 20 mole percent of calcium oxide; and
 from about 1 mole percent to about 20 mole percent of calcium carbide.
5. A solid solution of:
 from about 75 mole percent to about 98 mole percent of an oxide of a metal selected from the group consisting of zirconium, thorium, and hafnium;
 from about 1 mole percent to about 20 mole percent of an oxide of an element of either of groups IIA or IIIB of the periodic table of the elements; and
 from about 1 mole percent to about 20 mole percent of the sulfide of an element of either of groups IIA or IIIB of the periodic table of the elements.
6. A solid solution of:
 from about 75 mole percent to about 98 mole percent of an oxide of a metal selected from the group consisting of zirconium, thorium, and hafnium;
 from about 1 mole percent to about 20 mole percent of an oxide of an element of either of groups IIA or IIIB of the periodic table of the elements; and
 from about 1 mole percent to about 20 mole percent of the carbide of an element of either of groups IIA or IIIB of the periodic table of the elements.
7. A solid solution of:
 the oxide of either zirconium, thorium, or hafnium;
 the oxide of an element of either of groups IIA or IIIB of the periodic table of the elements; and
 either the sulfide or the carbide of said element of either of groups IIA or IIIB.
8. The solid solution of claim 7 containing the carbide of said element of either of Groups IIA or IIIB.
9. A method of manufacturing a metal from a melt comprising:
 monitoring the amount of carbon in said melt by contacting said melt with the solid solution of claims 2, 4, 6, or 8; and
 modifying the composition of said melt in response to said monitoring.
10. The solid solution of claim 7 containing the sulfide of said element of either of Groups IIA or IIIB.

11. A method of manufacturing a metal from a melt comprising:
monitoring the amount of sulfur in said melt by contacting said melt with the solid solution of claims 1, 3, 5, or 10; and
modifying the composition of said melt in response to said monitoring.

12. A method of manufacturing melt from a melt comprising contacting said melt with the solid solution of claims 1, 2, 3, 4, 5, 6 or 7.

13. A process for the detection of sulfur in a fluid comprising:
contacting said fluid with an electrolyte comprising a solid solution of:
from about 75 mole percent to about 98 mole percent of zirconium dioxide;
from about 1 mole percent to about 20 mole percent calcium oxide;
from about 1 mole percent to about 20 mole percent calcium sulfide;
providing a reference electrode in contact with said electrolyte; and
detecting electrical potential between said electrolyte and said electrode.

14. The process of claim 13 wherein said reference electrode comprises a solid solution of a metal and its metallic sulfide.

15. The process of claim 14 wherein said metal is an element of group VI B or VII B of the periodic table of the elements.

16. The process of claim 13 wherein said reference electrode comprises a solid solution of tungsten-tungsten sulfide, chromium-chromium sulfide or manganese-manganese sulfide.

17. The process of claim 13 wherein said electrolyte comprises:
from about 85 mole percent to about 96 mole percent zirconium dioxide;
from about 2 to about 10 mole percent calcium oxide; and
from about 2 to about 10 mole percent calcium sulfide.

18. The process of claim 13, 14, 15, 16 or 17 wherein said fluid is a molten metal.

19. The process of claim 17 wherein said molten metal is steel.

20. The process of claim 13 wherein said fluid comprises at least about 1 ppm of oxygen.

21. A process for the detection of sulfur in a fluid comprising:
contacting said fluid with an electrolyte comprising a solid solution of:
from about 75 mole percent to about 98 mole percent of thorium dioxide;
from about 1 mole percent to about 20 mole percent calcium oxide;
from about 1 mole percent to about 20 mole percent calcium sulfide;
providing a reference electrode in contact with said electrode; and
detecting electrical potential between said electrolyte and said electrode.

22. The process of claim 21 wherein said reference electrode comprises a solid solution of a metal and its metallic sulfide.

23. The process of claim 22 wherein said metal is an element of group VI B or VII B of the periodic table of the elements.

24. The process of claim 21 wherein said reference electrode comprises a solid solution of tungsten-tungsten sulfide, chromium-chromium sulfide or manganese-manganese sulfide.

25. The process of claim 21 wherein said electrolyte comprises:
from about 85 mole percent to about 96 mole percent thorium dioxide;
from about 2 to about 10 mole percent calcium oxide; and
from about 2 to about 10 mole percent calcium sulfide.

26. The process of claim 21, 22, 23, 24 or 25 wherein said fluid is a molten metal.

27. The process of claim 26 wherein said molten metal is steel.

28. The process of claim 21 wherein said fluid comprises at least about 1 ppm of oxygen.

29. A process for the detection of carbon in a fluid comprising:
contacting said fluid with an electrolyte comprising a solid solution of:
from about 75 mole percent to about 98 mole percent of zirconium dioxide;
from about 1 mole percent to about 20 mole percent calcium oxide;
from about 1 mole percent to about 20 mole percent calcium carbide;
providing a reference electrode in contact with said electrolyte; and
detecting electrical potential between said electrolyte and said electrode.

30. The process of claim 29 wherein said reference electrode comprises a solid solution of a metal and its metallic carbide.

31. The process of claim 30 wherein said metal is an element of group VI B or VII B of the periodic table of the elements.

32. The process of claim 29 wherein said reference electrode comprises a solid solution of tungsten-tungsten carbide, chromium-chromium carbide or manganese-manganese carbide.

33. The process of claim 29 wherein said electrolyte comprises:
from about 85 mole percent to about 96 mole percent zirconium dioxide;
from about 2 to about 10 mole percent calcium oxide; and
from about 2 to about 10 mole percent calcium carbide.

34. The process of claim 29, 30, 31, 32 or 33 wherein said fluid is a molten metal.

35. The process of claim 34 wherein said molten metal is steel.

36. The process of claim 29 wherein said fluid comprises at least about 1 ppm of oxygen.

37. A process for the detection of carbon in a fluid comprising:
contacting said fluid with an electrolyte comprising a solid solution of:
from about 75 mole percent to about 98 mole percent of thorium dioxide;
from about 1 mole percent to about 20 mole percent calcium oxide;
from about 1 mole percent to about 20 mole percent calcium carbide;
providing a reference electrode in contact with said electrolyte; and
detecting electrical potential between said electrolyte and said electrode.

38. The process of claim 37 wherein said reference electrode comprises a solid solution of a metal and its metallic carbide.

39. The process of claim 38 wherein said metal is an element of group VI B or VII B of the periodic table of the elements.

40. The process of claim 37 wherein said reference electrode comprises a solid solution of tungsten-tungsten carbide, chromium-chromium carbide or manganese-manganese carbide.

41. The process of claim 37 wherein said electrolyte comprises:
from about 85 mole percent to about 96 mole percent thorium dioxide;
from about 2 to about 10 mole percent calcium oxide; and
from about 2 to about 10 mole percent calcium carbide.

42. The process of claim 37, 38, 39, 40 or 41 wherein said fluid is a molten metal.

43. The process of claim 42 wherein said molten metal is steel.

44. The process of claim 37 wherein said fluid comprises at least about 1 ppm of oxygen.

45. Apparatus for the measurement of sulfur in a fluid comprising:
an electrolyte comprising:
from about 75 to about 98 mole percent of an oxide of a metal selected from the group consisting of zirconium, thorium, and hafnium;
from about 1 to about 20 mole percent of an oxide of an element of either of groups IIA or IIIB of the periodic table of the elements; and
from about 1 to about 20 mole percent of the sulfide of an element of either of groups IIA or IIIB of the periodic table of the elements.

46. Apparatus for the measurement of carbon in a fluid comprising:
an electrolyte comprising:
from about 75 to about 98 mole percent of an oxide of a metal selected from the group consisting of zirconium, thorium, and hafnium;
from about 1 to about 20 mole percent of an oxide of an element of either of groups IIA or IIIB of the periodic table of the elements; and
from about 1 to about 20 mole percent of he carbide of an element of either of groups IIA or IIIB of the periodic table of the elements.

47. An apparatus for the detection of sulfur in a fluid comprising:
an electrolyte comprising a solid solution of zirconium, hafnium, or thorium oxide;
an oxide of an element of either of groups IIA or IIIB of the periodic table of the elements; and
the sulfide of said element.

48. The apparatus of claim 47 further comprising a reference electrode in contact with said electrolyte.

49. The apparatus of claim 48 further comprising a first electrical contact connected to said reference electrode and a second electrical contact adapted for contact with said fluid.

50. The apparatus of claim 49 wherein said first and second electrical contacts are adapted for cooperation with an electric potential measuring means.

51. The apparatus of claim 48 wherein said reference electrode is isolated from physical contact with said fluid by a holder means.

52. The apparatus of claim 48 wherein said reference electrode comprises a solid solution of a metal and its metallic sulfide.

53. The apparatus of claim 52 wherein said metal is an element of group VI B or VII B of the periodic table of the elements.

54. The apparatus of claim 48 wherein said reference electrode comprises a solid solution of tungsten-tungsten sulfide; chromium-chromium sulfide or manganese-manganese sulfide.

55. The apparatus of claim 47 wherein:
said zirconium, hafnium, or thorium oxide is present in an amount of from about 75 to about 98 mole percent;
said oxide of an element is present in an amount of from about 1 to about 20 mole percent; and
said sulfide is present in an amount of from about 1 to about 20 mole percent.

56. The apparatus of claim 47 wherein:
said zirconium, hafnium, or thorium oxide is present in an amount of from about 85 to about 96 mole percent;
said oxide of an element is present in an amount of from about 2 to about 10 mole percent; and
said sulfide is present in an amount of from about 2 to about 10 mole percent.

57. An apparatus for the detection of carbon in a fluid comprising:
an electrolyte comprising a solid solution of zirconium, hafnium, or thorium oxide;
an oxide of an element of either of groups IIA or IIIB of the periodic table of the elements; and
the carbide of said element.

58. The apparatus of claim 57 further comprising a reference electrode in contact with said electrolyte.

59. The apparatus of claim 58 further comprising a first electrical contact connected to said reference electrode and a second electrical contact adapted for contact with said fluid.

60. The apparatus of claim 59 wherein said first and second electrical contacts are adapted for cooperation with an electric potential measuring means.

61. The apparatus of claim 58 wherein said reference electrode is isolated from physical contact with said fluid by a holder means.

62. The apparatus of claim 58 wherein said reference electrode comprises a solid solution of a metal and its metallic carbide.

63. The apparatus of claim 62 wherein said metal is an element of group VI B or VII B of the periodic table of the elements.

64. The apparatus of claim 58 wherein said reference electrode comprises a solid solution of tungsten-tungsten carbide; chromium-chromium carbide or manganese-manganese carbide.

65. The apparatus of claim 57 wherein:
said zirconium, hafnium, or thorium oxide is present in an amount of from about 75 to about 98 mole percent;
said oxide of an element is present in an amount of from about 1 to about 20 mole percent; and
said carbide is present in an amount of from about 1 to about 20 mole percent.

66. The apparatus of claim 57 wherein:
said zirconium, hafnium, or thorium oxide is present in an amount of from about 85 to about 96 mole percent;
said oxide of an element is present in an amount of from about 2 to about 10 mole percent; and
said sulfide is present in an amount of from about 2 to about 10 mole percent.

* * * * *

UNITED STATES PATENT AND TRADEMARK OFFICE
CERTIFICATE OF CORRECTION

PATENT NO. : 4,428,770

DATED : January 31, 1984

INVENTOR(S) : Wayne L. Worrell, et al

It is certified that error appears in the above-identified patent and that said Letters Patent is hereby corrected as shown below:

Column 1, line 8, inserted as the first sentence under "Background of the Invention" -- Certain rights may be retained by the U.S. Governement in regards to this invention pursuant to grant DMR-78-05937 awarded by the National Science Foundation. --

Signed and Sealed this

Twenty-second Day of June, 1993

Attest:

MICHAEL K. KIRK

Attesting Officer     Acting Commissioner of Patents and Trademarks